(12) United States Patent
Weijand et al.

(10) Patent No.: US 6,305,381 B1
(45) Date of Patent: *Oct. 23, 2001

(54) SYSTEM FOR LOCATING IMPLANTABLE MEDICAL DEVICE

(75) Inventors: Koen J. Weijand, Rockanje (NL); Markus Haller, Begnins (CH); Marty Bakx, Geleen; Robert Leinders, Limbricht, both of (NL); Todd Goblish; Jon Werder, both of Maple Grove, MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/239,306

(22) Filed: Jan. 29, 1999

Related U.S. Application Data

(63) Continuation-in-part of application No. 09/017,198, filed on Feb. 2, 1998, now Pat. No. 6,009,878.

(51) Int. Cl.[7] .................................................. A61B 19/00
(52) U.S. Cl. ............................................ 128/899; 600/424
(58) Field of Search .................................. 128/897–899; 600/424; 607/154

(56) References Cited

U.S. PATENT DOCUMENTS

| | | | |
|---|---|---|---|
| 4,441,498 | 4/1984 | Nordling | 128/419 P |
| 4,542,532 | 9/1985 | McQuilkin | 455/78 |
| 4,757,816 | 7/1988 | Ryan et al. | 128/419 PT |
| 4,760,837 | 8/1988 | Petit | 128/1 R |
| 5,006,115 | 4/1991 | McDonald | 604/175 |
| 5,009,644 | 4/1991 | McDonald | 604/175 |
| 5,099,845 | * 3/1992 | Besz et al. | 600/424 |
| 5,171,228 | 12/1992 | McDonald | 604/175 |
| 6,009,878 | * 1/2000 | Weijand et al. | 600/424 X |

* cited by examiner

Primary Examiner—John P. Lacyk
Assistant Examiner—Ryan Carter
(74) Attorney, Agent, or Firm—Thomas F. Woods; Michael J. Jaro; Harold Patton

(57) ABSTRACT

A system and method for locating an implantable medical device. The system consists of a flat "pancake" antenna coil positioned concentric with the implantable medical device target, e.g. the drug reservoir septum. The system further features a three location antenna array which is separate from the implantable device and external to the patient. The antenna array features three or more separate antennas which are used to sense the energy emitted from the implanted antenna coil. The system further features a processor to process the energy ducted by the antenna array. The system senses the proximity to the implant coil and, thus, the implant device by determining when an equal amount of energy is present in each of the antennas of the antenna array and if each such ducted energy is greater than a predetermined minimum. When such a condition is met, the antenna array is aligned with the implant coil. Thus the needle port through the antenna array is lined up with the septum of the drug reservoir. Alternative embodiments are further disclosed in which the processor and antenna array are positioned within the implanted device while the coil is external to the patient.

18 Claims, 11 Drawing Sheets

SYSTEM FOR LOCATING IMPLANTABLE MEDICAL DEVICE

RELATED APPLICATIONS

This application is a Continuation-in-Part of U.S. application 09/017,198 filed Feb. 2, 1998 now U.S. Pat. No. 6,009,878 and entitled "System For Locating Implantable Medical Device."

FIELD OF THE INVENTION

The present invention relates to implantable medical devices and, particularly, to an implantable medical device system for locating an implantable medical device with a high degree of precision.

BACKGROUND OF THE INVENTION

Many implantable medical devices require percutaneous communication. That is, in particular regard to implantable drug infusion devices, such devices often require the drug supply to be replenished. Typically, such replenishment is accomplished by inserting a needle through the skin and into the septum of a drug reservoir in such a device.

Because such a device is implanted and thus not able to be directly seen, care must be taken to ensure that the needle is properly placed into the device before injection. If the needle misses the device and, in particular, misses the drug reservoir in the device, the drugs will be immediately dispensed in the body, having potentially dire consequences for the patient. Moreover, if the needle is not fully placed through the septum and into the drug reservoir, the drug reservoir will not be adequately filled, also having potentially dire consequences for the patient.

Previous attempts have been made to accurately locate and identify implanted devices and, in particular, septum loading to the drug reservoir of implantable drug infusion devices. For example, Celcontrol, Inc. advertised an implantable vascular access device which required the attachment of an electrode to the skin and the attachment of a wire to the hypodermic needle to create a circuit for locating the implantable device. Such a system, besides having more complexity than desired, did not provide an accurate location of the needle in relation to the device without first inserting the needle through the skin. U.S. Pat. No. 5,171,228 disclosed a further system which required an RF transmitter and a transmitting antenna. Such a system, to date, has not proven practical or provided an acceptable precision for locating the implantable device. Thus, there exists a need for a simple device and technique for sensing the position of an implanted device and, in particular, of a drug reservoir septum, without first requiring the skin to be punctured or additional electrode attachments to be made to the patient.

SUMMARY OF THE INVENTION

These and other objects are accomplished by the present invention which includes a system and method for locating an implantable medical device. The system consists of a flat "pancake" antenna coil positioned concentric with the implantable medical device target, e.g. the drug reservoir septum. The system further features a three location antenna array which is separate from the implantable device and external to the patient. The antenna array features three or more separate antennas which are used to sense the energy emitted from the implanted antenna coil. The system further features a processor to process the energy ducted by the antenna array. The system senses the proximity to the implant coil and, thus, the implant device by determining when an equal amount of energy is present in each of the antennas of the antenna array and if each such ducted energy is greater than a predetermined minimum. When such a condition is met, the antenna array is aligned with the implant coil. Thus the needle port through the antenna array is lined up with the septum of the drug reservoir. Alternative embodiments are further disclosed in which the processor and antenna array are positioned within the implanted device while the coil is external to the patient.

The FIGS. are not necessarily to scale.

DETAILED DESCRIPTION OF THE INVENTION

Figure 1:
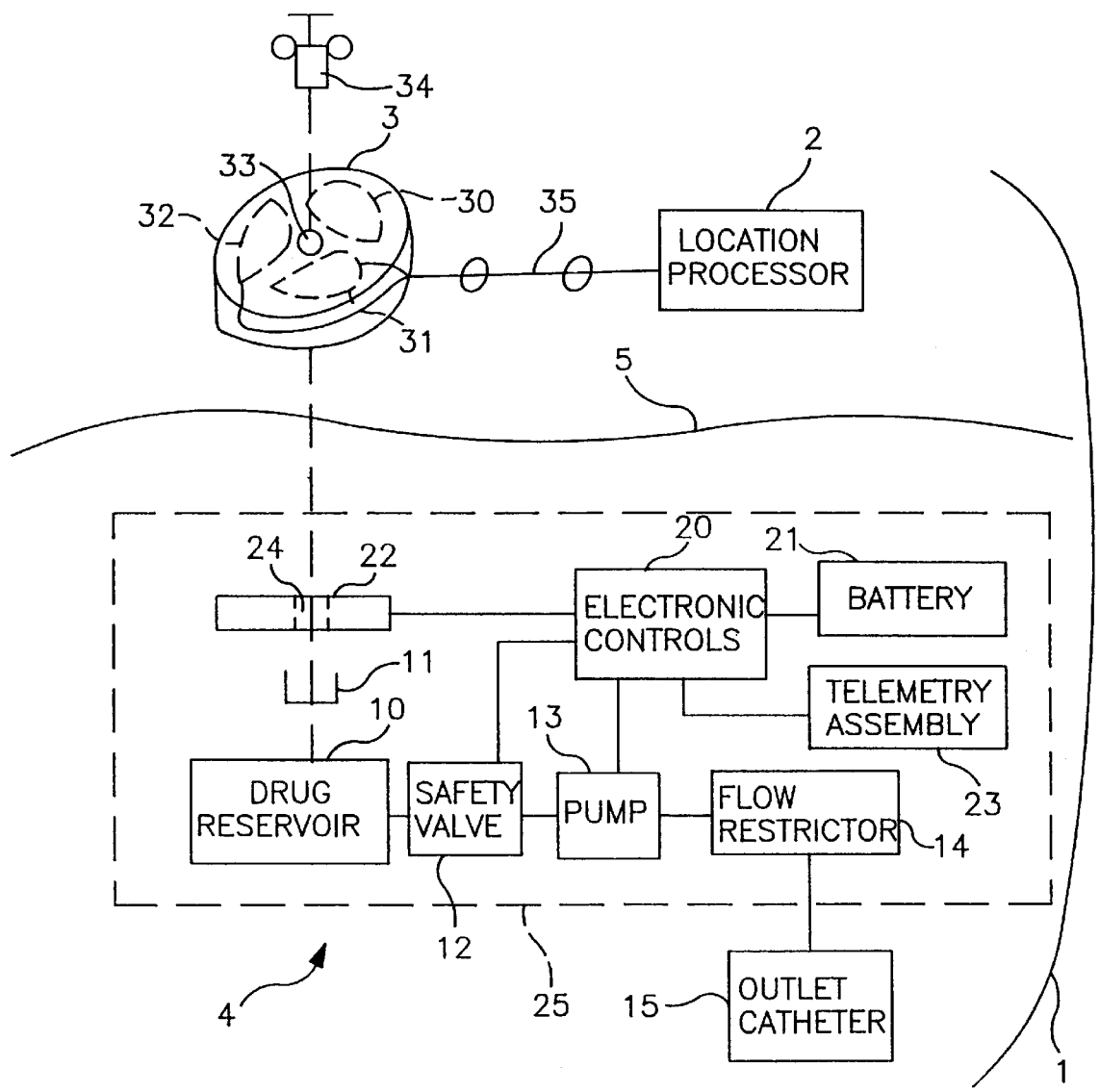
FIG. 1 is a block diagram showing the system according to the present invention.

FIG. 1 is a block diagram showing the system according to the present invention. As seen, the system 1 features a location processor 2 coupled to implant location antenna array 3 which are used to locate implantable medical device 4 positioned beneath skin of patient 5. Medical device 4 may be of any design desired, such as the Medtronic SynchroMed implantable drug pump, although other devices besides drug pumps may also be used. In the preferred embodiment device 4 includes a drug reservoir 10 having a septum 11 for drug replenishment. Drug reservoir outlets such drugs, past pump 13 to outlet catheter 15. In an additional embodiment (although illustrated here for clarity) the device could further feature a safety valve 12 and , beyond flow restrictor 14, constructed according to the United States patent application entitled "Implantable Drug Infusion Device Having A Safety Valve" of Markus Haller and Koen Weijand (Our File: P-7354 (including P-7329)) and United States patent application entitled "Implantable Drug Infusion Device Having A Flow Regulator" of Markus Haller, Phillipe Renaud and Christian Amacker (Our File: P-7322 (Including P-7353)) respectively both of which filed Feb. 2, 1998 and incorporated herein by reference. Electronic controls 20 powered by battery 21 provide control and energy to pump and safety valve and further to provide control and energy to implant coil 22. Device further includes a telemetry assembly 23 to provide two-way communication between device 4 and any suitable external device. As seen, implant coil 22 is positioned such that opening 24 therein is aligned with septum 11. Coil is aligned with opening centered therein. In this view implant coil is shown positioned above septum, although implant coil may also be positioned around or, indeed, beneath the septum. What is important is for coil and thus opening and septum to be aligned. As further seen, all elements of the device but the outlet catheter are housed within the hermetic enclosure 25 as is well known in the art.

As further seen in this figure, implant location antenna array 3 is movably positioned outside of patient 5. Array features three air coil antennas 30, 31 and 32 symmetrically disposed about the guide 33 and all mounted within the same plane. As seen, guide 33 is provided to permit a needle 34 to be positioned through array and thus into and past septum 11 to thereby replenish drugs in the reservoir. Each antenna is electrically coupled to location processor through a series of wires, commonly designated 35.

Figure 2A:
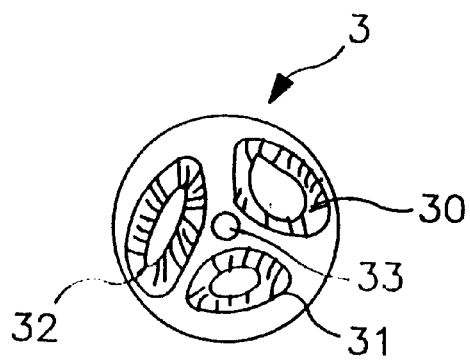
FIGS. 2A and 2B are a top view of array.
Figure 2B:
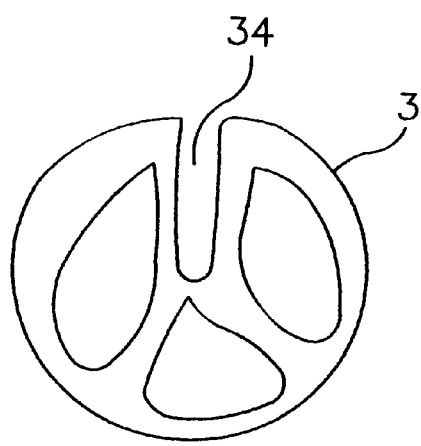

Turning now to FIG. 2A which shows a top view of array 3, as seen, antennas 30, 31 and 32 are symmetrically disposed about guide 33. Antennas, moreover, are also disposed along the same plane. Each antenna is identical, and is constructed as an planar air coil antenna, preferably from printed wiring board, although other antenna constructions may be used, such as a ferrite coil. The planar antenna is housed within a non-conductive material, such as plastic. Guide is disposed in a center location and is sized to permit a needle to be passed therethrough. Although shown as a circular passage, a needle slot 34 may further be provided, as shown in FIG. 2B. As discussed above, antenna is positioned external to the patient and is designed to be moved along the surface of the patient's body to thereby accurately locate the implant coil and thus the septum of the device.

Figure 3A:
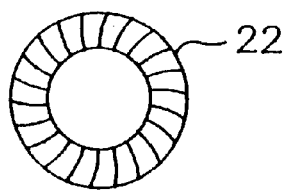
FIG. 3A is a top view of implant coil.
Figure 3B:
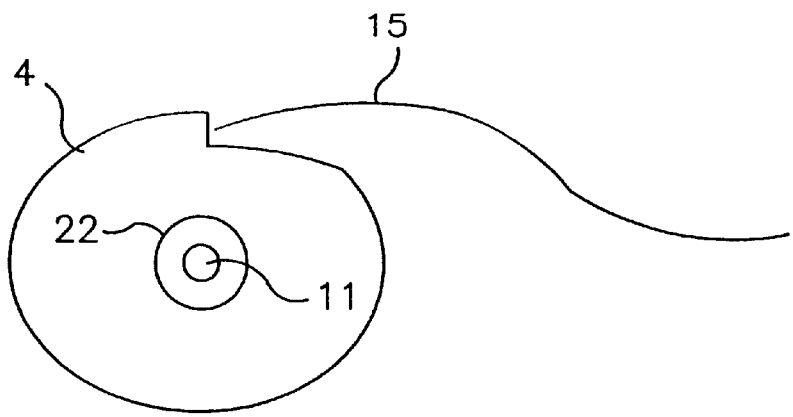
FIG. 3B depicts the implant coil positioned coaxial with the septum of device.
Figure 3C:
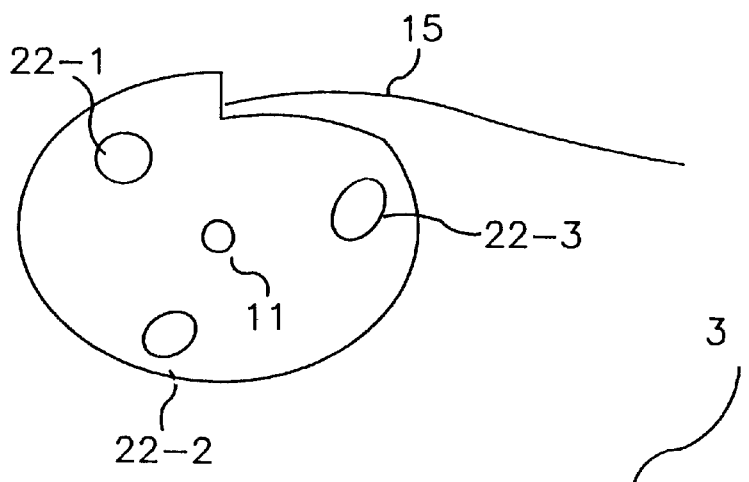
FIG. 3C depicts an alternative configuration of implant coils.
Figure 3D:
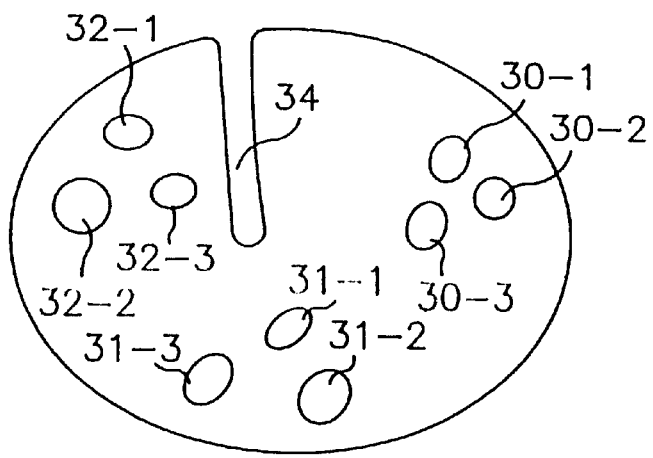
FIG. 3D depicts an alternative configuration of array.

FIG. 3A is a top view of implant coil 22. Implant coil is constructed of any acceptable material. Although shown in FIG. 1 as a separate coil and device it should be appreciated that implant coil could also be fashioned by using an implant telemetry of the device as is well known to one skilled in the art. FIG. 3B depicts the implant coil 22 positioned coaxial with the septum 11 of device 4. FIG. 3C depicts a device 4 which features an alternative configuration of coil. In particular in this embodiment a series of coils 22-1, 22-2 and 22-3 are used. Such plurality of coils may be used to each emit at a differing frequencies so that the array not only may accurately sense the septum's location, but also the proper orientation of the array to the device may also be detected. As seen in FIG. 3D in this embodiment the array 3 would feature a series of matching sensing arrays 30-1, 30-2, 30-3; 31-1, 31-2, 31-3; 32 -1, 32-2, 32-3 of antennas, each series attuned to sense the output of the corresponding coil. While this embodiment is a bit more complicated than that shown above, it provides the same function without having to locate the coil around the septum.

Figure 4:
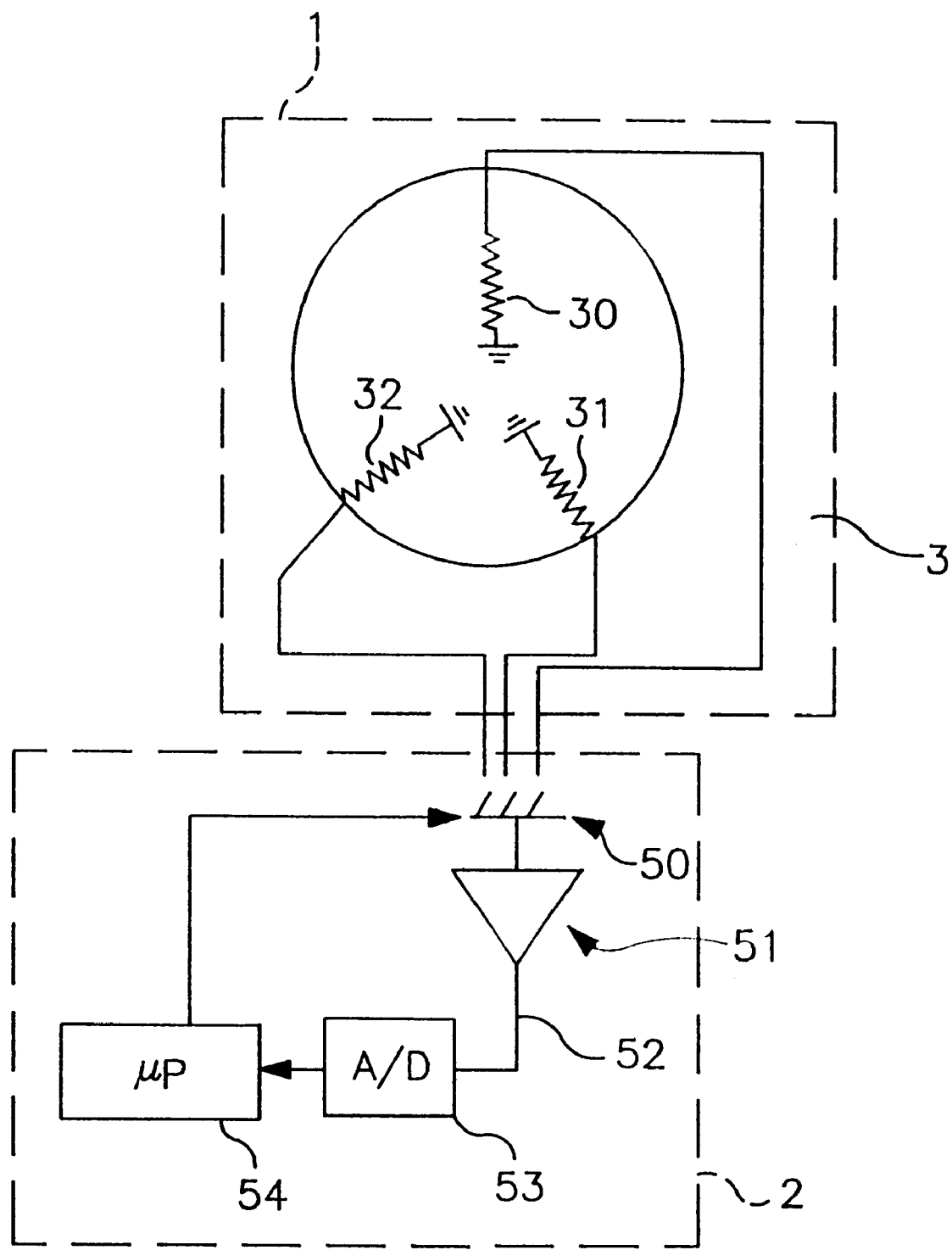
FIG. 4 discloses the circuit used in the location processor.

FIG. 4 discloses the circuit used in the location processor 2 and array 3. As seen, antennas 30, 31 and 32 disposed in array 3 are coupled into location processor 2 through switch 50. Through such a coupling this embodiment uses a sampling technique to alternatingly sample the signal on each antenna. Each such sampled signal is then passed through amplifier 51 which also provides a filtering function and outputs the signal on line 52 as an RSSI. In the preferred embodiment, amplifier is preferably NE604, available from National Semiconductor Corporation, 2900 Semiconductor Drive, P.O. Box 58090, Santa Clara, Calif., 95052-8090. Signal is then processed through analog digital computer 53 where it is then put into the microprocessor 54. Microprocessor thereafter compares each of the signals sampled from the antennas and determines whether the energy received by each of the antennas is above a predetermined minimum. In such a case an operating range signal is emitted to indicate to the operator the operating distance with the implanted device, as discussed in more detail below. Microprocessor would then determine whether the same amount of energy is being sensed by each antenna, which, due to the geometry of implant coil 22 and array 3, indicates the antennas having a guide therein as well as implant coil are thus in alignment. Microprocessor would then cause to be emitted an alignment signal. As discussed in more detail below, in an alternate embodiment, rather than using a sampling technique to detect the energy sensed by each antenna, the system could also use a technique in which each coil is oppositely coupled, that is in anti-phase, such that when a null is sensed the coils are each sensing an equal amount of energy.

Figure 5:
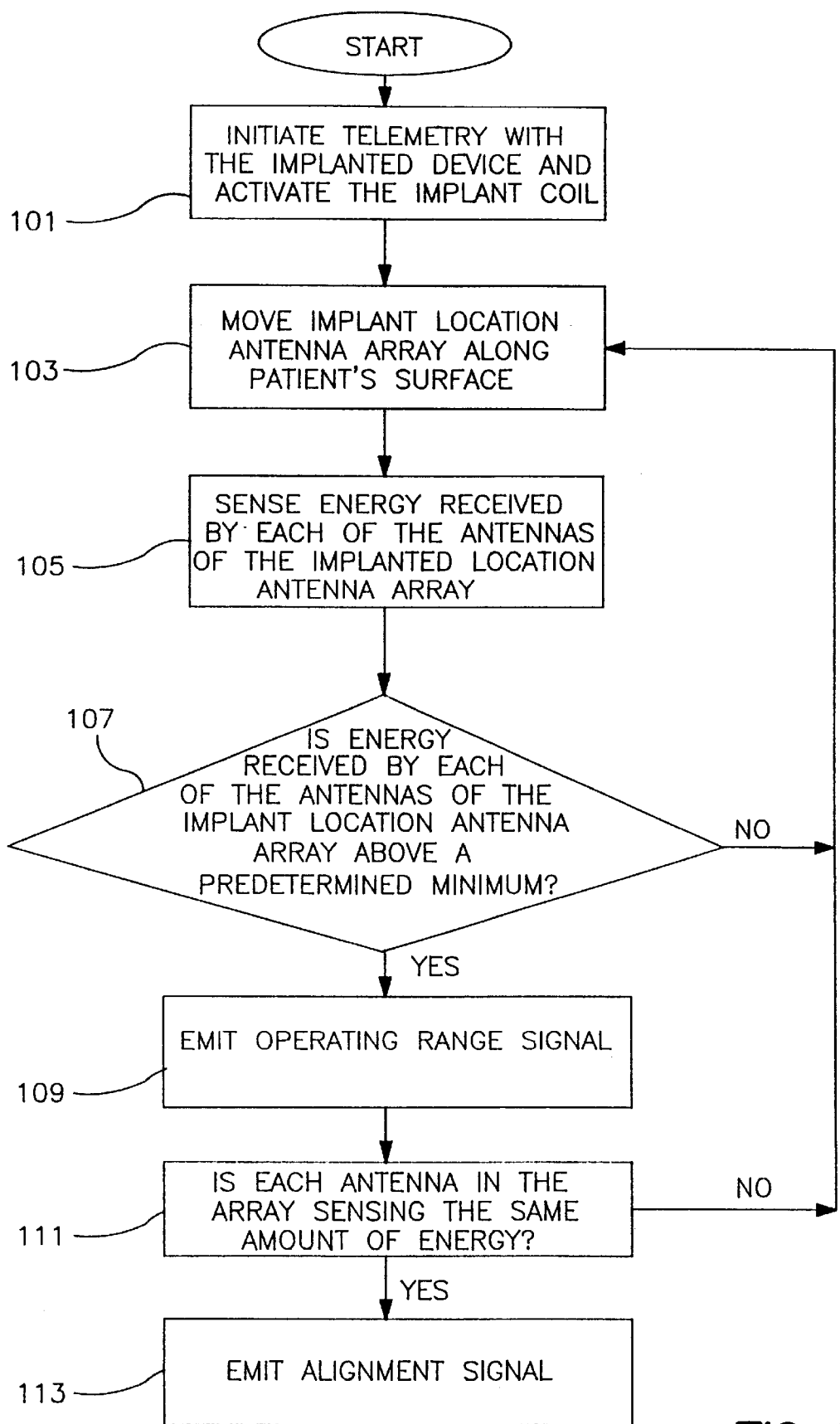
FIG. 5 discloses the procedure used to locate a device according to the present invention.

FIG. 5 discloses the procedure used to locate a device according to the present invention. As seen at 101, telemetry is initiated with the implant device. Such telemetry initiation is done to instruct the implant device to activate the implant coil. In the preferred embodiment the implant coil is activated to thereby transmit energy at a known frequency, preferably the device transmits at 32.768 kHz since this frequency is readily available in present implantable pulse generators. Next, at 103 the implant location antenna array is moved along the patient's surface. Next, at 105 the energy received by each of the antennas of the implant location antenna array is sensed. Next, at 107 device determines if such energy is above a predetermined minimum. As can be appreciated, this predetermined minimum amount of energy required to be sensed by each antenna dictates the furthest distance the antenna of the array may be from the implant coil, and still provide information regarding the location of the coil and thus the device. Although determining whether the energy sensed by each antenna is above a predetermined threshold is shown as a separate step, this could also be integrated within another step. Next, if the energy sensed is above a predetermined minimum the device goes to step 109 and emits an operating range signal, otherwise the device recycles back to step 103. Next, at 111 a comparison is made to determine if each of the antennas in the array are sensing the same amount of energy. Comparison may be made using a sampling technique, as described above in FIG. 4, or a non-sampling technique, as described below with regard to FIG. 6. With either or any other technique, if it is found each of the antennas is sensing an equal amount of energy, then if the antennas each are sensing the same amount of energy which is above the predetermined minimum, then this implies each of the antennas are positioned an equal distance away from the implant coil. Because the passage and septum are located directly centered within the array and the coil respectively, this than means that they are in alignment. Next, at 113 a signal is emitted by the location processor to indicate such alignment. The emitted signal is preferably a light, although this may also be delivered through a sound or both. In a further embodiment the array or the device may additionally feature a vibration device, which is either activated or deactivated (whichever is desired) upon alignment. Through such a manner the transmission of energy from the coil to the array may be used to precisely align the components.

Figure 6:
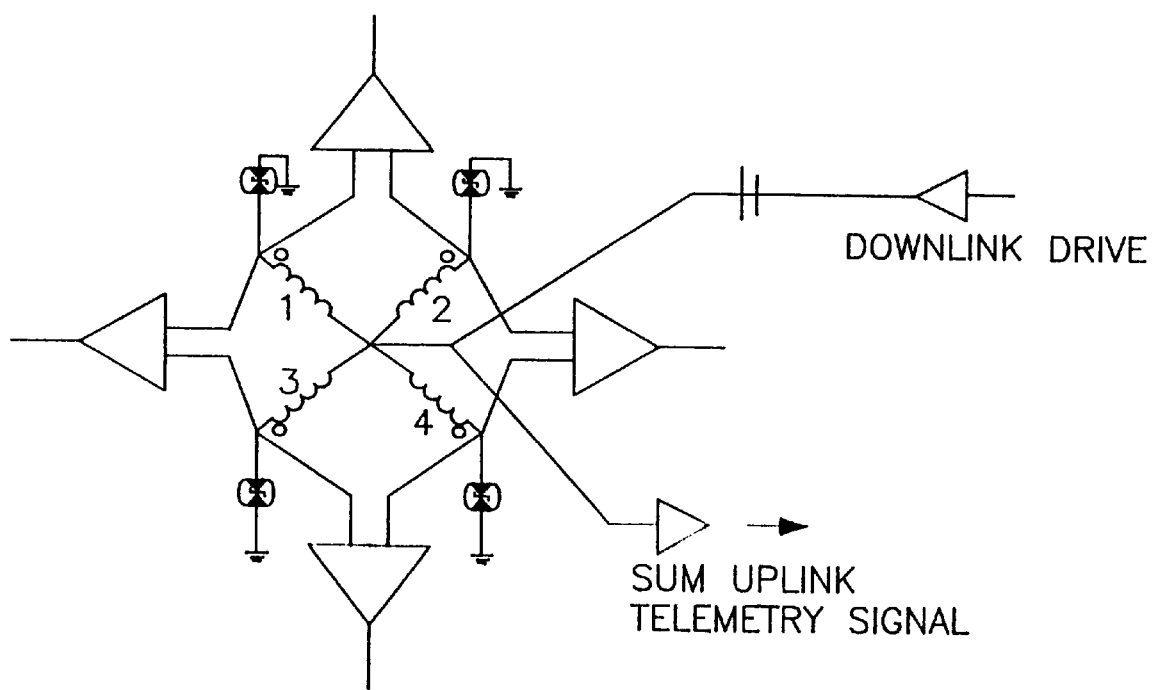
FIG. 6 discloses an alternative circuit for use in the location processor.

FIG. 6 discloses an alternative circuit for use in the location processor 2. As seen in this embodiment four separate antennas are used in the array. Each coil is further connected to the associated electronics such that the voltages from the coils are subtracted. The center connection of the coils provides the sum of the signals sensed by all the coils. Because the signal from two coils connected in anti-phase is only zero, the symmetry line of these coils crosses the center of the transmitting antenna, in this case the implant coils 22. This means that all four signals derived are zero, the four symmetry lines of these antennas are crossing the center of the implant coil. In addition, the sum signal must be the maximum, or at least greater than the predetermined value, thereby indicating the antenna is in connection with an implant coil. As already discussed above, this determines that the device is within a predetermined operating range. Although shown as having four antennas, this embodiment may further be constructed using any number of antennas, from 3 to 360, for example. Among the advantages believed offered by such a configuration is the ability to combine both device telemetry and localization.

Figure 7:
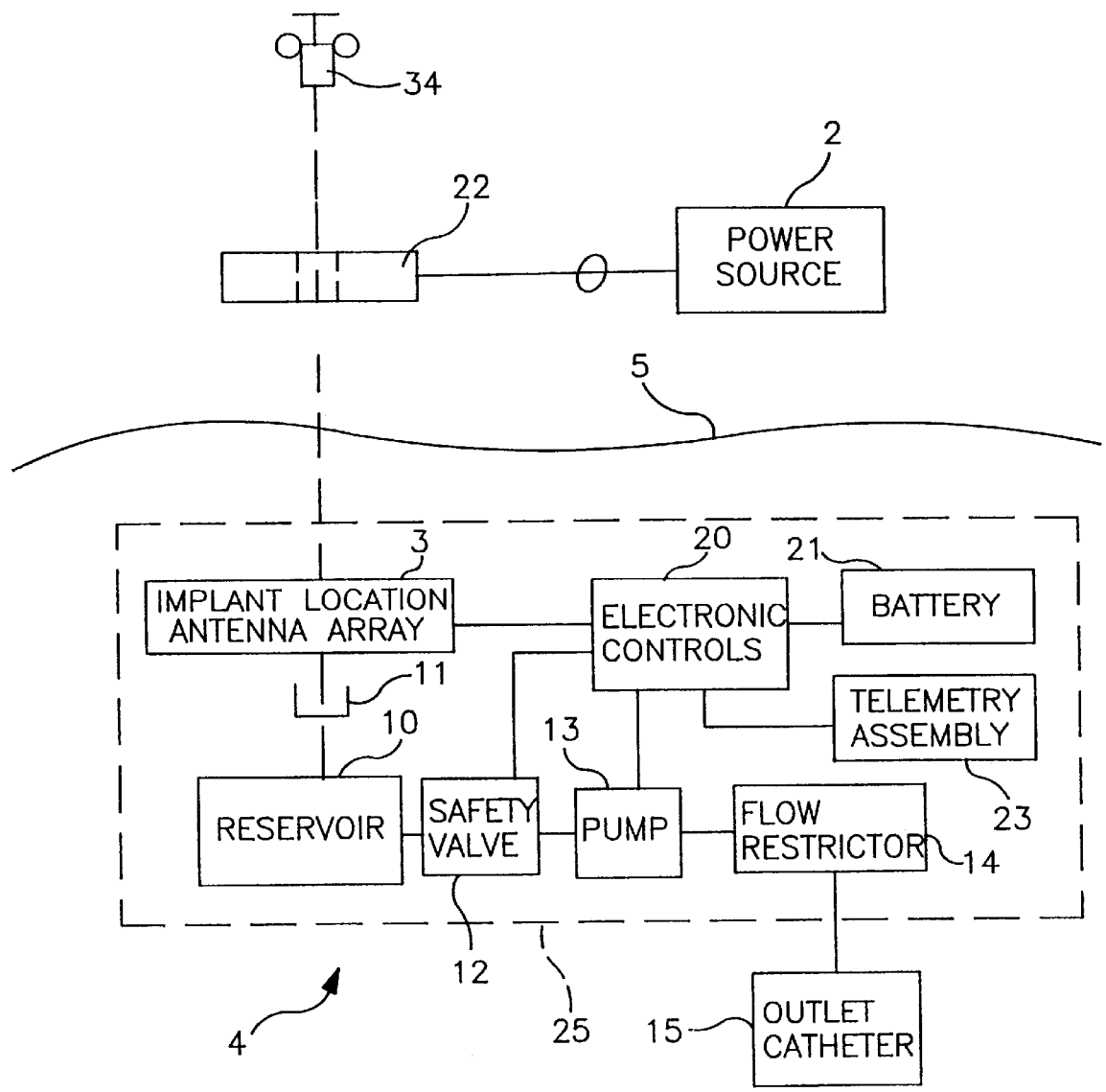
FIG. 7 is a block diagram showing an alternative system according to the present invention.

FIG. 7 is a block diagram showing an alternative system according to the present invention. As seen this system differs from that disclosed in FIG. 1 in that the location processor 2 coupled to implant location antenna array 3 are integrated within the device 4 while the coil 22 is featured outside of the patient. Like the system of FIG. 1, device 4 may still be of any design desired. Device may include a drug reservoir 10 having a septum 11 for drug replenishment. Drug reservoir outlets such drugs through safety valve 12, past pump 13, beyond flow restrictor 14 to outlet catheter 15. Electronic controls 20 powered by battery 21 provide control and energy to pump and safety valve and further to provide control and energy to implant coil 22. Device further includes a telemetry assembly 23 to provide two-way communication between device 4 and any suitable external device. In this embodiment, array 3 (rather than implant coil 22 as shown in FIG. 1) is positioned such that a guide 33 therein is aligned with septum 11. In this view array 3 is shown positioned above septum, although array 3 may also be positioned around or, indeed, beneath the septum. As already discussed above, what is important is for array 3 and in particular guide 33 and septum to be aligned, As further seen, all elements of the device but the outlet catheter are housed within the hermetic enclosure 25 as is well known in the art. As further seen, coil 22 is movably positioned outside of patient 5. Coil 22 is of the same design discussed above, and features an opening 24 (either a slot or a hole) therein to permit a needle 34 to be positioned through array and thus into and past septum 11 to thereby replenish drugs in the reservoir. In a still further embodiment a refill the syringe can be constructed having an integral coil.

Figure 8:
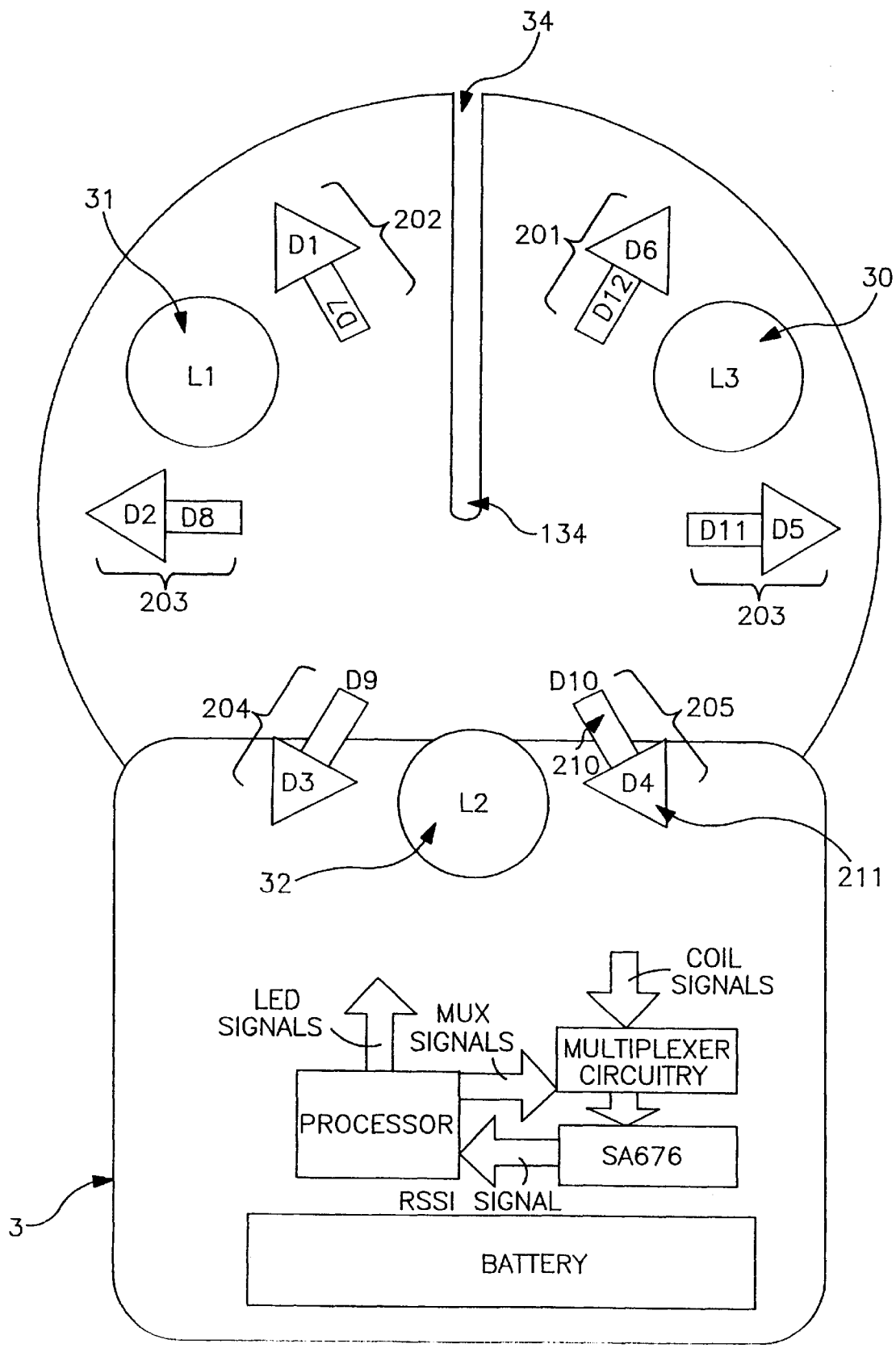
FIGS. 8 and 9 depict an alternative embodiment of the present invention.
Figure 9:
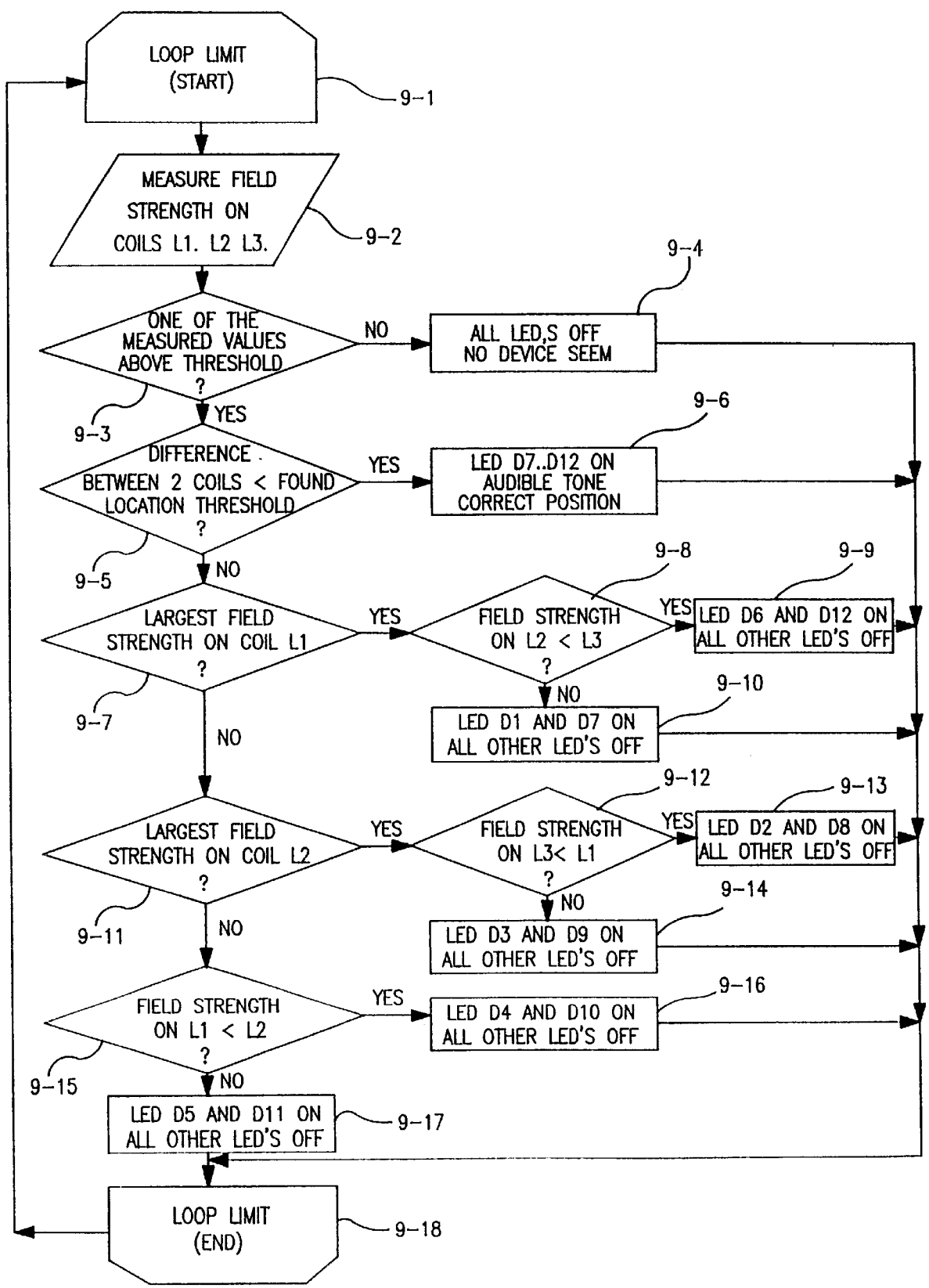

FIGS. 8 and 9 depict an alternative embodiment of the present invention, in particular, an embodiment featuring a guiding mechanism system for locating implantable medical device. As already discussed above, the present invention permits the locating implantable medical device through the sensing of an equal amount of energy on each of the antennas of the antenna array. When such an equal amount of energy is sensed, then the external locator and the implant coil are aligned. This additional alternative embodiment includes a method and apparatus which features a guiding mechanism system for locating implantable medical device. In particular, the sensed energy on each of the antennas of the antenna array are used as the input parameters for a routine which determines the way the user has to move the external locator in order to align with the implanted medical device. The direction in which to move the external device may be given by visual and/or audible indication to the user. In the preferred embodiment of this embodiment this is done by illuminating a tail and an arrow LED to point to the direction to move the locator. Whenever the correct position is found, only the tail LED's are illuminated. A possible mechanical setup is shown in FIG. 8. A flowchart for the guiding routine can be found in FIG. 9.

FIG. 8 depicts a mechanical set up for septum locating array 3 according to the alternative embodiment. As seen in this embodiment, array includes a guide slot 34 which, as discussed above, reaches into a midpoint 134 between the various sensing coils, 30, 31, 32. In this embodiment, array further features a series of directional indication signals 200–205. Referring to 205, in particular, each signal includes both a tail portion 210 and a head portion 211. Head and tail portions are selectively illuminated to provide information to the user in which direction the array should be moved, thus, when D5 and D11, in the present embodiment, are illuminated, the array should be moved to the right. Once center portion 134 is properly positioned above the septum, and each of the coils sense an equal amount of energy as described above, signals would be illuminated such that only the tail portions would be lit. Thus, head and tail portions are only illuminated when movement is required; only tail portions are illuminated when no movement is required to properly locate center portion 134 relative to septum. As discussed above, although illumination of such signals is preferred, for this alternative embodiment other indications may also be provided, including audible outputs or, in fact, tangible outputs, such as vibration.

FIG. 9 is a flow chart which illustrates a guiding routine for the illumination of the signals depicted in FIG. 8. As seen at 9-1, the routine is begun and the field strength in coils L1 (31), L2 (32) and L3 (30) is carried out at 9-2. At 9-3 a determination is made whether one of the measured values is above the preset threshold (see 2 in FIG. 10). If such threshold is not met, then the device proceeds to 9-4 where all LED signals (in the preferred embodiment) are kept turned off indicating that no device is seen. If a measured value is above the predetermined threshold, then the routine drops to 9-5 once the difference between two coils is measured. If this measured difference is less than the preselected found location threshold (see 1 in FIG. 10), then the routine proceeds to block 9-6 where only the tail portions of each of the signals is turned on and all other portions of the signals, such as the head, are turned off thereby indicating direct position has been found. If permitted, at this stage, an audible tone or tactile response may also be communicated to the user. If the difference between two coils is greater than the found location threshold in block 9-5, then the device proceeds to block 9-7. At 9-7 the device determines whether the largest field strength is seen in coil L1 (31). If it is, then the device proceeds to block 9-8 and determined whether the field strength in L2 (32) is less than the field strength in coil L3 (30). If yes, then the device proceeds to block 9-9 in which signals D6 and D12 are turned on while all other LEDs are kept off. Through this illumination the user is permitted to further move the device in the direction shown by the illumination 201, referring again to FIG. 8. If the field strength in coil L2 (32) is not less than L3 (30), then the device proceeds to block 9-10 and turns on the signals LEDs D1 and D7 while keeping all other LEDs off. In a similar manner the device uses the steps shown in blocks 9-12, 9-13 and 9-14 if the largest field strength on coil L2 (32) is detected as shown in block 9-11.

Finally, the device proceeds to step 9-15 and determines whether the filed strength in L1 (31) is less than L2 (32). If yes, then the device proceeds to 9-16 and illuminates head and tail portions of signal 205. If the field strength in L1 (31)

is greater or equal than L2 (32), then the device instead proceeds to block 9-17 and turns on head and tail portions of signal 200. Thereafter the device drops down to 9-18 and the routine loops back to the beginning of the loop (step 9-1).

Figure 10:
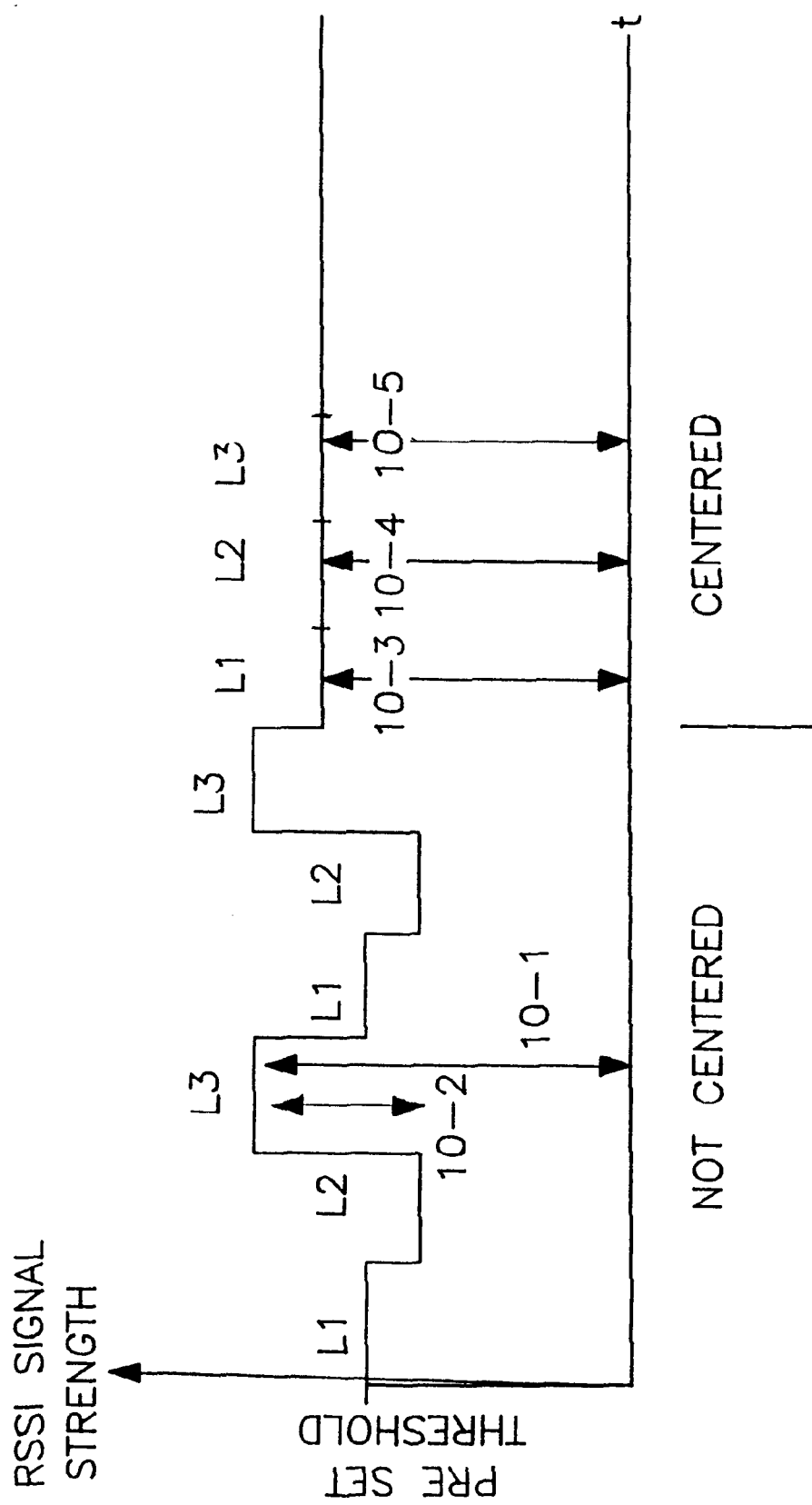
FIG. 10 shows the measured RSSI signal when septum locator is off centered.

FIG. 10 depicts the measured signals sensed in the RSSI when the antenna array is off-centered from the septum. As discussed already with regards to FIG. 9, among the first processes performed by the device is determine whether any one of the measured values on coils L1, L2 or L3 is above the preset threshold. As shown, the amplitude on coil L3 of FIG. 10 is above the preset threshold. Thus, the block 9-3, referring again to FIG. 9, is satisfied and further analysis of the sensed signal strength may be performed.

In the current illustration this means that an analysis is performed on the difference between any two of the coils. If the difference between any two of the coils is greater than the preset found location threshold, then the device is not centered. This is shown here as difference 10-2, between the coils L3 and L2. Essentially, because this difference is greater than the predefined found location threshold, the coils are not sensing signals at roughly similar strengths. This would indicate the coils are thus not centered around the transmission coil, positioned above the septum in the preferred embodiment. When the coils L1, L2 and L3 do, however, get put in a position central to the transmitting coil, then this found location threshold corresponding to the difference in signal strength sensed by any of the two coils approaches zero. This is shown also in this figure, namely, in the section in which the amplitude for sections L1, L2 and L3, depicted as lines 10-3, 10-4, 10-5 are almost exactly the same. This indicates these coils are centered about the transmitting coil.

In the preferred embodiment, incidentally, each coil is measured once every 64 ms for a period of no less than 21 ms.

Figure 11:
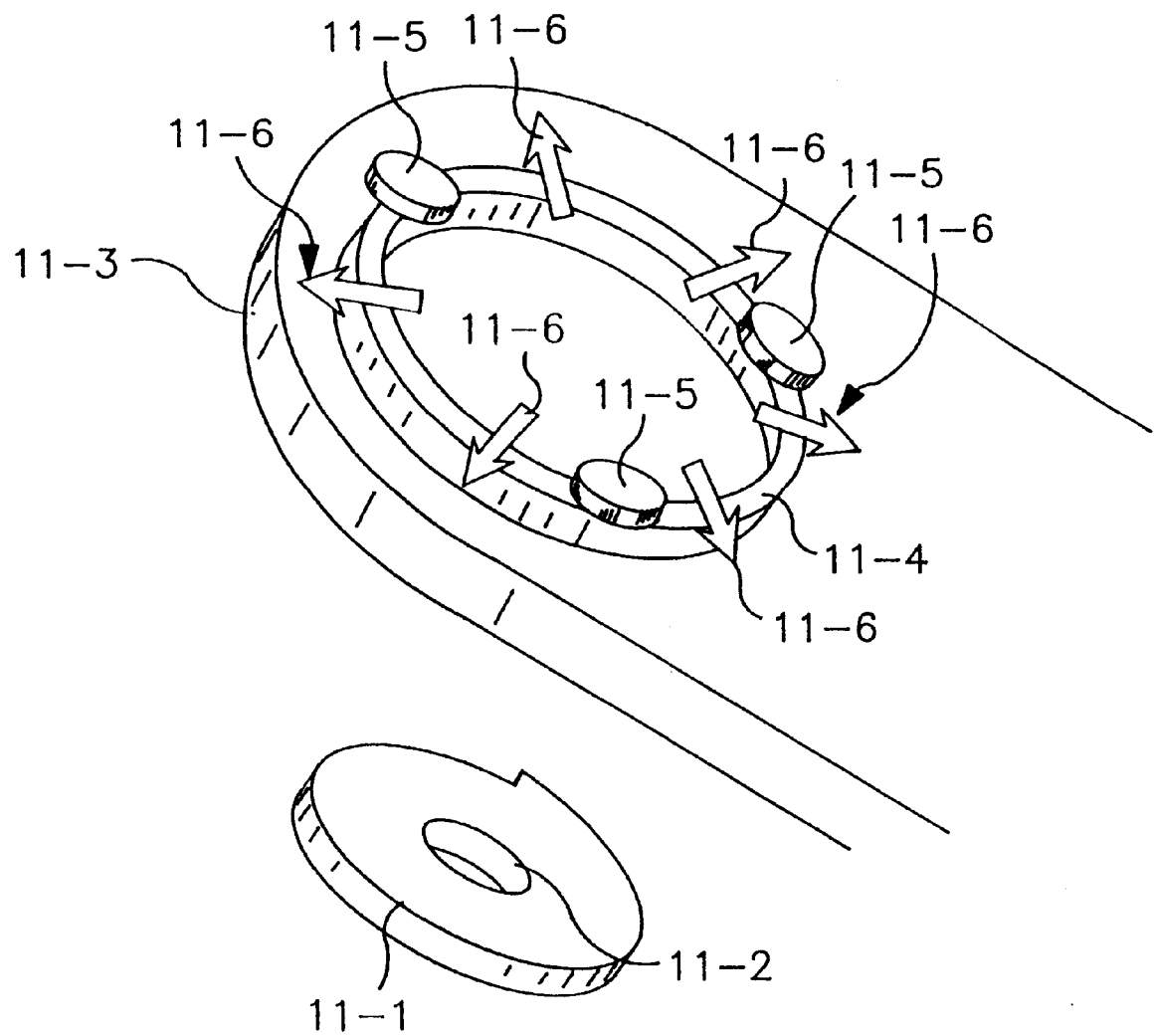
FIG. 11 is a further alternative embodiment of the present invention.

In a still further embodiment, the location detecting system may be further used to accurately locate the optimal position of a recharger to recharge a rechargeable medical device. In such a system, shown in FIG. 11, the IPG 11-1 features a recharge coil 11-2, to receive recharge energy from a recharger. The recharge coil, however, may also be used to first emit a location signal for detection by an array. The recharger 11-3 carries either a separate recharging coil 11-4 and position coils 11-5, which, in turn, are used to activate position indicators 11-6 as described above. Once the optimal position for the device relative to the recharger are determined, the recharging coil 11-4 coil may thereafter be used to deliver recharge energy to the recharge coil and thus to the implanted device. In an alternative design, one or more of the position coils 11-5 may be used in place of a dedicated recharging coil to deliver recharge energy to the IPG. In operation, a rough location can be established by feeling the device. The IPG can start sending the location signal once it has detected that some level of recharge field is present. The external device should alternate its charge to allow reception of the transmitted signal from the IPG and in that way allow for a window to determine the optimal location for the recharge of the device. A magnet can also be used to switch on the signal in the IPG but this assumes that there is still some supply voltage left in the IPG. The location signal does not have to be alternated on and off like the recharge and can be on during the complete recharge cycle. The recharge coil's output for the purpose of signaling device location is triggered through a magnet or by programming initiation.

Although a specific embodiment of the invention has been disclosed, this is done for purposes of illustration and is not intended to be limiting with regard to the scope of the invention. Thus the present invention as disclosed provides a method and system for accurately locating an implanted device, and in particular a septum within an implanted device, without first requiring the patient's skin to be punctured. Although the invention is described as having a separate external positioning array through which a needle is inserted, the invention may also be incorporated as a part of a needle assembly. It is contemplated various other substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A system for locating an implantable medical device, comprising:
   the implantable device, the device comprising:
   a transmitter capable of generating output signals;
   a coil array comprising a first receiving coil, a second receiving coil and a third receiving coil, the coils emitting sensed signals in response to receiving at least portions of the output signals, and
   a processor operably coupled to the first, second and third coils to receive the sensed signals, the processor determining the respective levels of energy sensed by the first, second and third coils, the processor intermittently determining the level of energy received by the first, second and third receiving coils, the processor further comprising means for determining whether the level of energy sensed by the first coil, the second coil or the third coil exceeds a predetermined threshold level.

2. A system for locating an imlantable medical device, comprising:
   the implantable device, the device comprising:
   transmitter capable of generating output signals;
   a coil array comprising a first receiving coil and a second receiving coil, the coils emitting sensed signals in response to receiving at least portions of the output signals, and
   a processor operably coupled to the first and second coils to receive the sensed signals, the processor determining the respective levels of energy sensed by the first and second coils, the processor intermittently determining the level of energy received by the first and second receiving coils, the processor further comprising means for determining whether the level of energy sensed by the first coil or the second coil exceeds a predetermined threshold level.

3. A system according to claim 2, wherein the coil array further comprises means for signaling the direction of the transmitter relative to the coil array.

4. A system according to claim 3, wherein the means for direction signaling is operably coupled to the processor, the processor further comprising means for selectively activating the signaling means.

5. A system according to claim 4, wherein the signaling means comprises a series of illuminated arrows.

6. A system according to claim 5, wherein the illuminated arrows comprise a tail portion and a head portion, the head portion being separately illuminable from the tail portion.

7. A system according to claim either of claims 1 or 2, wherein the processor further comprises means for determining whether the respective levels of energy sensed by the individual coils are substantially the same.

8. A system according to any of the preceding claims, wherein the implantable device comprises a drug delivery device, the drug delivery device comprising a drug reservoir, the drug reservoir comprising a drug reservoir septum through which the drug reservoir may be refilled.

9. A method of locating an implantable medical device comprising a transmitter configured to transmit output signals therefrom and a plurality of receiving antennae configured in an array, the receiving antennae being configured to receive at least portions of the output signals, the receiving antennae further being operably connected to at least one processor configured to receive at least portions of the output signals and the process such signals, the method comprising:

transmitting output signals from the transmitter;

moving the array along an exterior surface of a patient;

determining the relative levels of energy received by the individual antennae in the array;

determining whether the levels of energy received by the individual antennae are substantially the same; and upon determining that the levels of energy received by the individual antennae are substantially the same, emitting a device location signal to an operator.

10. A method of locating an implantable medical device according to claim 9, wherein emitting a device location signal further comprises emitting a light signal.

11. A method of locating an implantable medical device according to claim 9, wherein emitting the device location signal commences upon a telemetry signal being received by the implantable device.

12. A method of locating an implantable medical device according to claim 9, wherein emitting the device location signal emitting energy further comprises activating an implant coil in the implantable medical device to transmit energy at a known frequency.

13. A method of locating an implantable medical device according to claim 9, wherein determining that the levels of energy received by the individual antennae are substantially the same further comprises determining if the energy levels received by the individual antennae exceeds a predetermined minimum level.

14. A method of locating an implantable medical device according to claim 13, further comprising emitting an operating range signal.

15. A method of locating an implantable medical device according to claim 9, wherein emitting the device location signal further comprises emitting a sound.

16. A method of locating an implantable device according to claim 9, further comprising providing a tactile feedback member to the array, the tactile feedback member being configured to provide a feedback output signal comprising at least a first feedback signal and a second feedback signal and, when the device location signal is emitted, changing the feedback outback signal from the first feedback signal to the second feedback signal.

17. A method of locating an implantable medical device according to claim 9, wherein the second feedback signal is a null signal.

18. A method of locating an implantable medical device according to claim 9, wherein the first feedback signal is a null signal.

* * * * *

UNITED STATES PATENT AND TRADEMARK OFFICE
CERTIFICATE OF CORRECTION

PATENT NO.    : 6,305,381 B1
DATED         : October 23, 2001
INVENTOR(S)   : Weijand et al.

It is certified that error appears in the above-identified patent and that said Letters Patent is hereby corrected as shown below:

Column 8,
Line 35, change "imlantable" to -- implantable --.
Line 38, change "transmitter" to -- a transmitter --.
Line 64, change "to claim either of claims 1 or 3" to -- to claim 1 or 2 --.
Line 38, change "and the process" to -- and process --.

Signed and Sealed this

Eighteenth Day of March, 2003

JAMES E. ROGAN
*Director of the United States Patent and Trademark Office*